US006895106B2

(12) United States Patent
Wang et al.

(10) Patent No.: US 6,895,106 B2
(45) Date of Patent: *May 17, 2005

(54) METHOD FOR STITCHING PARTIAL RADIATION IMAGES TO RECONSTRUCT A FULL IMAGE

(75) Inventors: Xiaohui Wang, Pittsford, NY (US); David H. Foos, Rochester, NY (US); James Doran, Rochester, NY (US); Michael K. Rogers, Mendon, NY (US)

(73) Assignee: Eastman Kodak Company, Rochester, NY (US)

( * ) Notice: Subject to any disclaimer, the term of this patent is extended or adjusted under 35 U.S.C. 154(b) by 642 days.

This patent is subject to a terminal disclaimer.

(21) Appl. No.: 09/950,544

(22) Filed: Sep. 11, 2001

(65) Prior Publication Data

US 2003/0048938 A1 Mar. 13, 2003

(51) Int. Cl.[7] .................................................. G06K 9/00
(52) U.S. Cl. ....................................... 382/132; 382/284
(58) Field of Search .................................. 382/128, 132, 382/199, 284, 289, 291, 293, 294, 296, 298; 378/62; 250/370.08, 370.09

(56) References Cited

U.S. PATENT DOCUMENTS

| 4,613,983 | A | | 9/1986 | Yedid et al. ................... 378/99 |
|---|---|---|---|---|
| 5,123,056 | A | * | 6/1992 | Wilson ............................ 382/6 |
| 5,833,607 | A | * | 11/1998 | Chou et al. .................. 600/407 |
| 5,986,279 | A | | 11/1999 | Dewaele ....................... 250/582 |
| 6,459,094 | B1 | * | 10/2002 | Wang et al. ................. 250/584 |
| 6,563,943 | B1 | * | 5/2003 | Sasada ......................... 382/132 |
| 6,600,831 | B1 | * | 7/2003 | Sasada ......................... 382/132 |
| 6,714,680 | B1 | * | 3/2004 | Sasada ......................... 382/216 |
| 6,757,418 | B2 | * | 6/2004 | Wei et al. .................... 382/132 |

FOREIGN PATENT DOCUMENTS

| EP | 0 866 342 A1 | 9/1998 | ............. G01T/1/29 |
|---|---|---|---|
| EP | 0 919 856 A1 | 6/1999 | ............ G03B/42/02 |
| EP | 0 919 858 A1 | 6/1999 | ............ G03B/42/02 |

(Continued)

*Primary Examiner*—Andrew W. Johns
(74) *Attorney, Agent, or Firm*—William F. Noval

(57) ABSTRACT

A method of forming a composite digital image comprising: providing 1–N digital images formed from 1–N contiguous segments of a larger radiographic image recorded in 1–N overlapping storage phosphor screens wherein N is equal to or greater than 2 and wherein the image content in the overlapped region of contiguous images is the same, and the end edge of a screen nearest an x-ray source is present in both contiguous images; selecting a pair of contiguous digital images, wherein one image is closer to said x-ray source than said other image; correcting for any geometric distortion if applicable in said pair of digital images based on the distance between x-ray source and said storage phosphor screen; determining any rotational displacement and any vertical displacement between said pair of digital images by matching said end edge of said one image present in said pair of images correcting for image orientation if applicable based on any said rotational displacement; determining any horizontal displacement between said pair of digital images by correlating the image content in said overlapping regions of said pair of digital images; stitching said pair of digital images together to form a larger composite digital image along said one image edge based on any said horizontal and vertical displacement; and repeating said correcting for any geometric distortion to said stitching with the larger composite image and the next consecutive overlapping digital image until all N digital images are stitched together to form a full composite image.

20 Claims, 9 Drawing Sheets

FOREIGN PATENT DOCUMENTS

| | | | |
|---|---|---|---|
| JP | 2000-232976 A | 8/2000 | ............ A61B/6/00 |
| JP | 2000-241920 A | 9/2000 | ............ G03B/42/04 |
| JP | 2000-250153 A | 9/2000 | ............ G03B/42/04 |
| JP | 2000-258861 A | 9/2000 | ............ G03B/42/02 |
| JP | 2000-267210 A | 9/2000 | ............ G03B/42/04 |
| JP | 2000-275760 A | 10/2000 | ............ G03B/42/02 |
| JP | 2000-275761 A | 10/2000 | ............ G03B/42/02 |
| JP | 2000-285252 A | 10/2000 | ............ G06T/11/80 |
| JP | 2000-339444 A | 12/2000 | ............. G06T/1/00 |
| JP | 2001-202507 A | 7/2001 | ............. G06T/3/00 |
| JP | 2001-274974 A | 10/2001 | ........... H04N/1/387 |
| JP | 2001-307085 A | 11/2001 | ............. G06T/3/00 |

\* cited by examiner

FIG. 1G
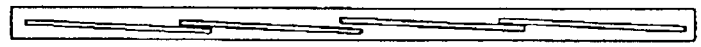
FIG. 1F
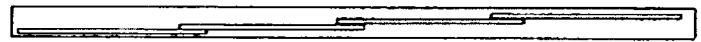
FIG. 1E
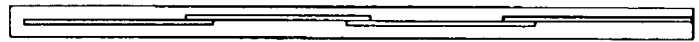
FIG. 1D
FIG. 1C
FIG. 1B
FIG. 1A

METHOD FOR STITCHING PARTIAL RADIATION IMAGES TO RECONSTRUCT A FULL IMAGE

FIELD OF THE INVENTION

This invention relates in general to digital radiography, and in particular to the imaging of a long human body part, such as the spine or legs, using a storage phosphor-based computed radiography system.

BACKGROUND OF THE INVENTION

When a long segment of the human body is imaged using the conventional screen-film technique, special cassettes and films of extended length are used, such as 30×90 cm and 35×105 cm. As medical institutions are migrating from analog screen-film systems to digital modalities, such as computed radiography (CR), these types of exams impose a significant challenge. This is because the size of digital detector is limited. For example, the largest CR storage phosphor cassette from several major CR vendors is limited to 35×43 cm, which can only image a portion of the long body part at a time. To address this problem, several methods have been proposed. European Patent EP0919856A1 discloses a way of staggering several storage phosphor cassettes together. The cassettes can be in the alternating (FIG. 1A), staircase-wise (FIG. 1B), or oblique (FIG. 1C) arrangement. During the x-ray exposure, all the partially overlapping cassettes are exposed simultaneously, therefore each storage phosphor screen that resides inside the corresponding cassette records a part of the image of the long body part. The drawback of this approach is that the metallic frames of the front (closer to the x-ray source) cassettes impose shadows in the image recorded in the back cassettes. The shadows are not removable and therefore may hinder diagnostic interpretation of the acquired images. European Patent EP0866342A1 (also U.S. Pat. No. 5,986,279, issued Nov. 16, 1999, inventor Dewaele) presents a method that is based on partially overlapping a plurality of storage phosphor screens for extended imaging coverage. The screens can also be configured in an alternating (FIG. 1D), staircase-wise (FIG. 1E), or oblique (FIG. 1F) overlapping arrangement. Further, the screens can be contained in a single, extended length cassette for convenience of use. This approach overcomes the drawback of the cassette stacking method because there are no cassette metallic frames present in the x-ray path. However, in practice, this method requires that the storage phosphor screens be removed from the cassettes before imaging, and to be placed back into the cassettes in a darkroom after the x-ray exposure, which is cumbersome in the clinical environment.

The sub-images acquired by the individual storage phosphor screens must be stitched together to create a composite full image. The stitched full image should be distortion-free for the purposes of diagnostic interpretation and geometric measurement. U.S. Pat. No. 4,613,983, issued Sep. 23, 1986, inventors Yedid et al., discloses a method to reconstruct a composite radiographic image from a set of sub-images. However, this method is applicable only when the relative position between the sub-images is precisely controlled by the acquisition hardware. For any of the configurations shown in FIG. 1, the variation in the placement of the cassettes/phosphor screens during the x-ray exposure or the variability of the CR reader in scanning the phosphor screens, causes non-deterministic translation and rotation displacements between the acquired sub-images. The displacements can vary slightly from one exam to the next; geometric compensation is required to correct for the rotation and translation displacements. In addition, geometric compensation is also required to correct for magnification distortion caused by variations in distance from the x-ray source to the cassette and storage phosphor screens. To address these problems, European Patent EP0919858A1 proposes a method that utilizes a pattern of reference markers that impose shadows simultaneously with the diagnostic image in each of the acquired sub-images. After the reference markers are identified in each sub-image, the image distortion is corrected based on the known marker locations. Translation and rotation displacements between the sub-images are also computed using the known marker locations. Once the geometric compensation processing is completed, the composite full image is reconstructed. The drawback of this method is that a precisely fabricated pattern of reference markers must be imaged simultaneously with the patient in order to achieve precise geometric registration of the sub-images. The shadow of the reference markers may obscure diagnostically important information in the stitched image.

It is therefore desirable to develop an image processing algorithm that can (1) automatically perform image demagnification, (2) automatically detect and correct the translation and rotation displacements between the sub-images, and (3) form a composite full image that has high geometric fidelity without relying on external reference markers.

SUMMARY OF THE INVENTION

According to the present invention, there is provided a solution to the problems discussed above.

According to a feature of the present invention, there is provided a method of forming a composite digital image comprising:

providing 1–N digital images formed from 1–N contiguous segments of a larger radiographic image recorded in 1–N overlapping storage phosphor screens wherein N is equal to or greater than 2 and wherein the image content in the overlapped region of contiguous images is the same, and the end edge of a screen nearest an x-ray source is present in both contiguous images;

selecting a pair of contiguous digital images, wherein one image is closer to said x-ray source than said other image;

correcting for any geometric distortion if applicable in said pair of digital images based on the distance between x-ray source and said storage phosphor screen;

determining any rotational displacement and any vertical displacement between said pair of digital images by matching said end edge of said one image present in said pair of images;

correcting for image orientation based on any said rotational displacement if applicable;

determining any horizontal displacement between said pair of digital images by correlating the image content in said overlapping regions of said pair of digital images;

stitching said pair of digital images together to form a larger composite digital image along said one image edge based on any said horizontal and vertical displacement; and repeating said correcting for any geometric distortion to said stitching with the larger composite image and the next consecutive overlapping digital image until all N digital images are stitched together to form a full composite image.

Advantageous Effect of the Invention

The invention has the following advantages.

1. Enables the generation of a composite full image from a plurality of sub-images without requiring the use of external reference markers to perform geometric distortion corrections.

2. Preserves a high degree of geometric accuracy in the stitched image.

3. Results in improved image quality in a reconstructed (composite) image by minimizing the presence of shadows of non-anatomic structures superimposed on the anatomic regions of interest.

BRIEF DESCRIPTION OF THE DRAWINGS

FIGS. 1A–1G are diagrammatic views of several multiple cassette-screen arrangements.

FIGS. 1A–1C shows a plurality of storage phosphor cassettes, with each cassette containing one storage phosphor screen, arranged in alternating, staircase-wise, and oblique positions, respectively. The storage phosphor screens are represented as solid vertical lines inside the cassettes. FIGS. 1D–1F shows a plurality of storage phosphor screens arranged in alternating, staircase-wise, and oblique positions, respectively. The screens can be contained within a single, extended length cassette. FIG. 1G shows a configuration consisting of a set of storage phosphor screens/cassettes that are placed in an alternating arrangement with the screens placed in front of the cassettes (closer to x-ray source).

The shadow of the middle screen top edge is recorded in image 301, and the shadow of the bottom edge is recorded in image 303.

Figure 3A:
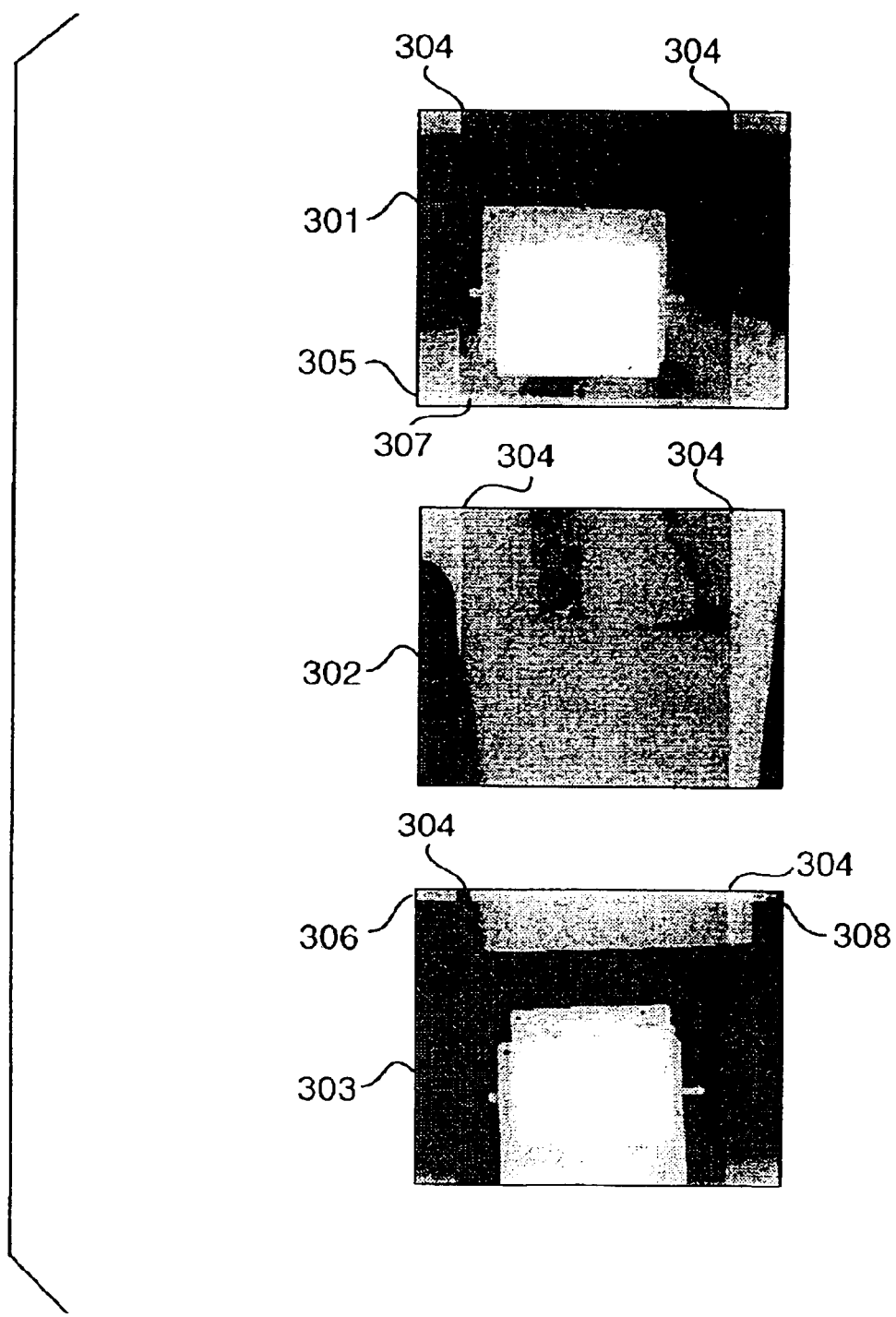
FIG. 3A is a diagrammatic view showing three sub-images acquired using any of the configurations shown in FIG. 1. The middle image 302 is recorded on a storage phosphor screen (either the screen itself or the screen within a cassette) that is placed closer to the x-ray source. The top image 301 and the bottom image 303 are recorded on two storage phosphor screens (either the screen itself or the screen within a cassette) that are placed behind the middle screen.
Figure 3B:
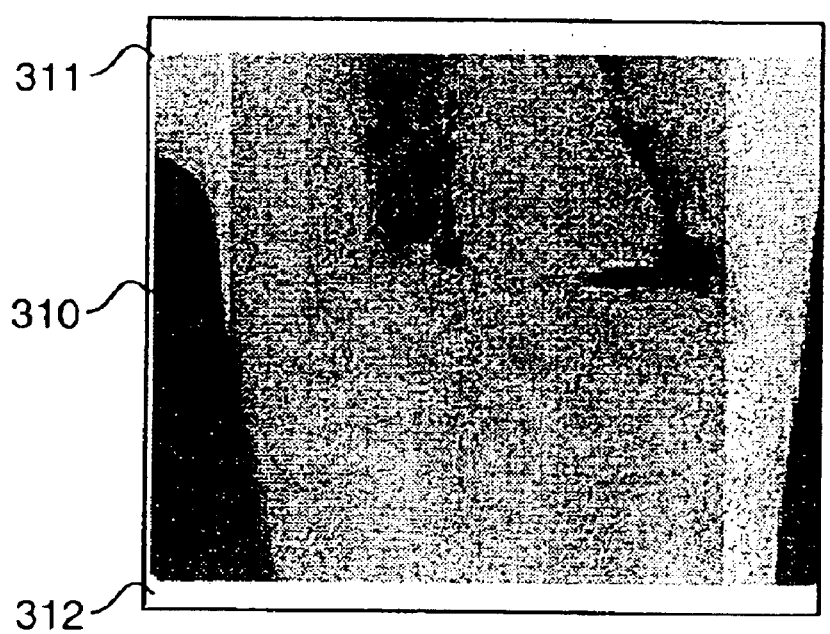

FIG. 3B is a modification of the middle image of FIG. 3A.

Figure 4B:
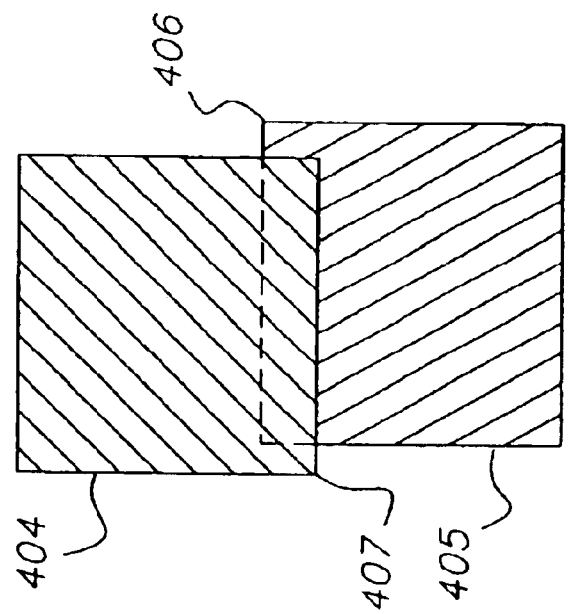
Figure 4A:
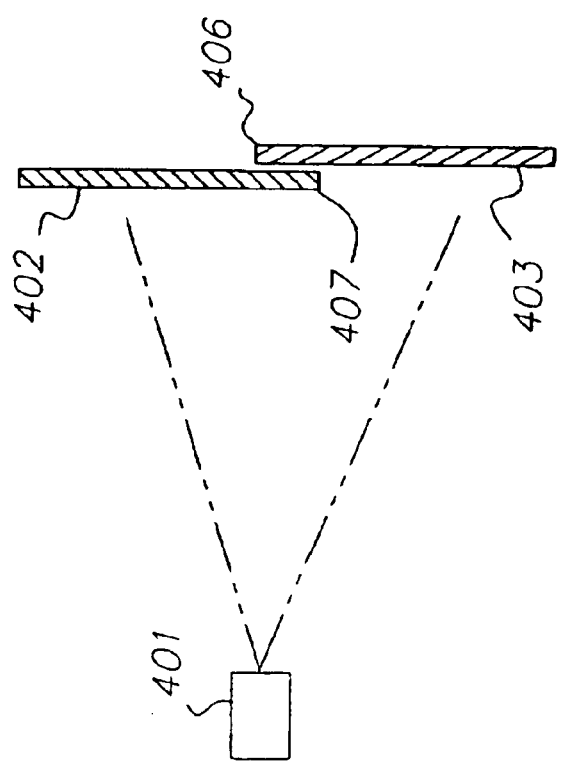

FIGS. 4A and 4B are diagrammatic views illustrating the definitions of the front screen, back screen, front screen overlap edge, and back screen overlap edge.

Figure 5:
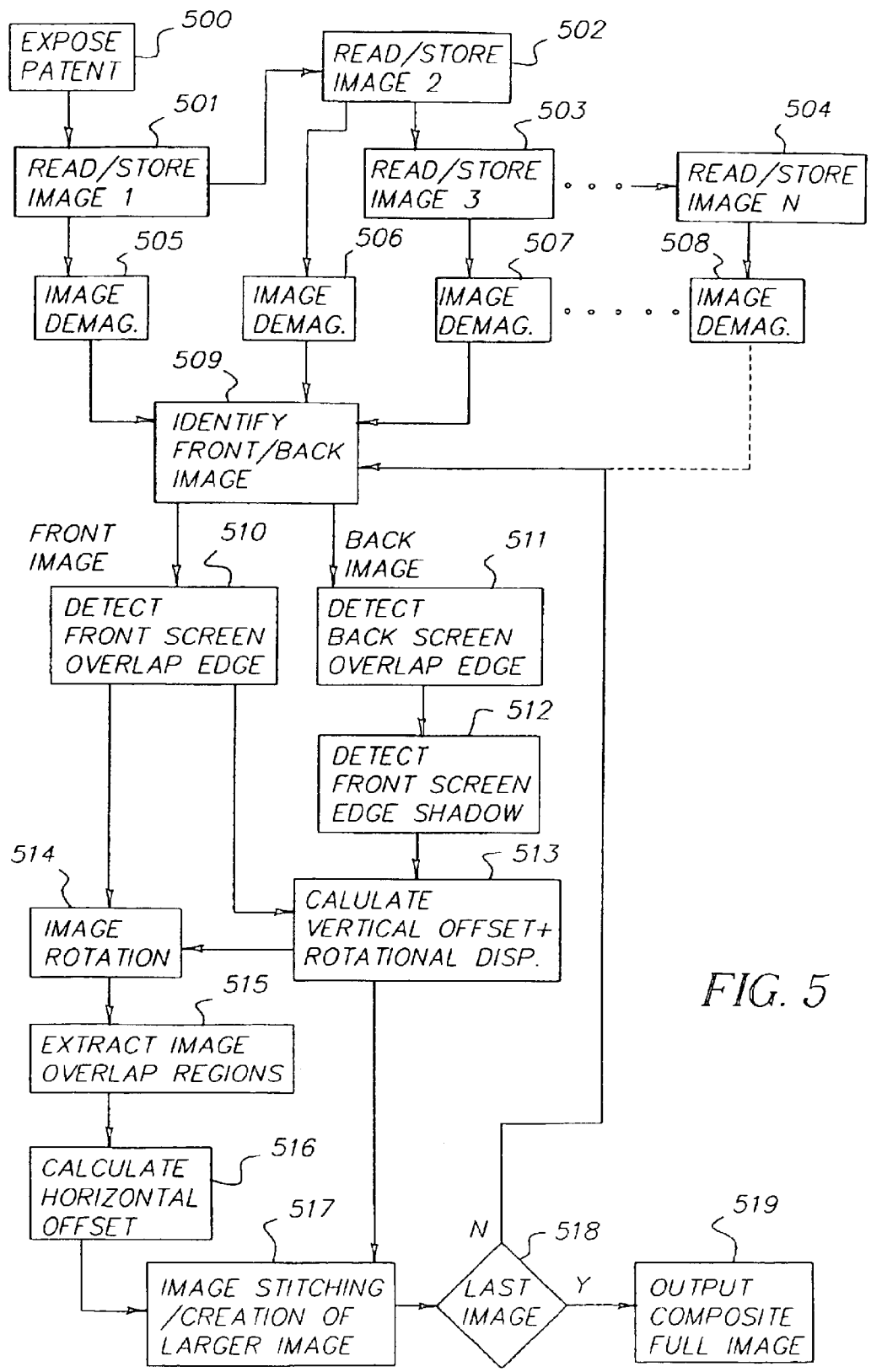

FIG. 5 is a flow diagram showing the image processing steps for automatic formation of a composite image from a plurality of images according to the present invention.

Figure 6:
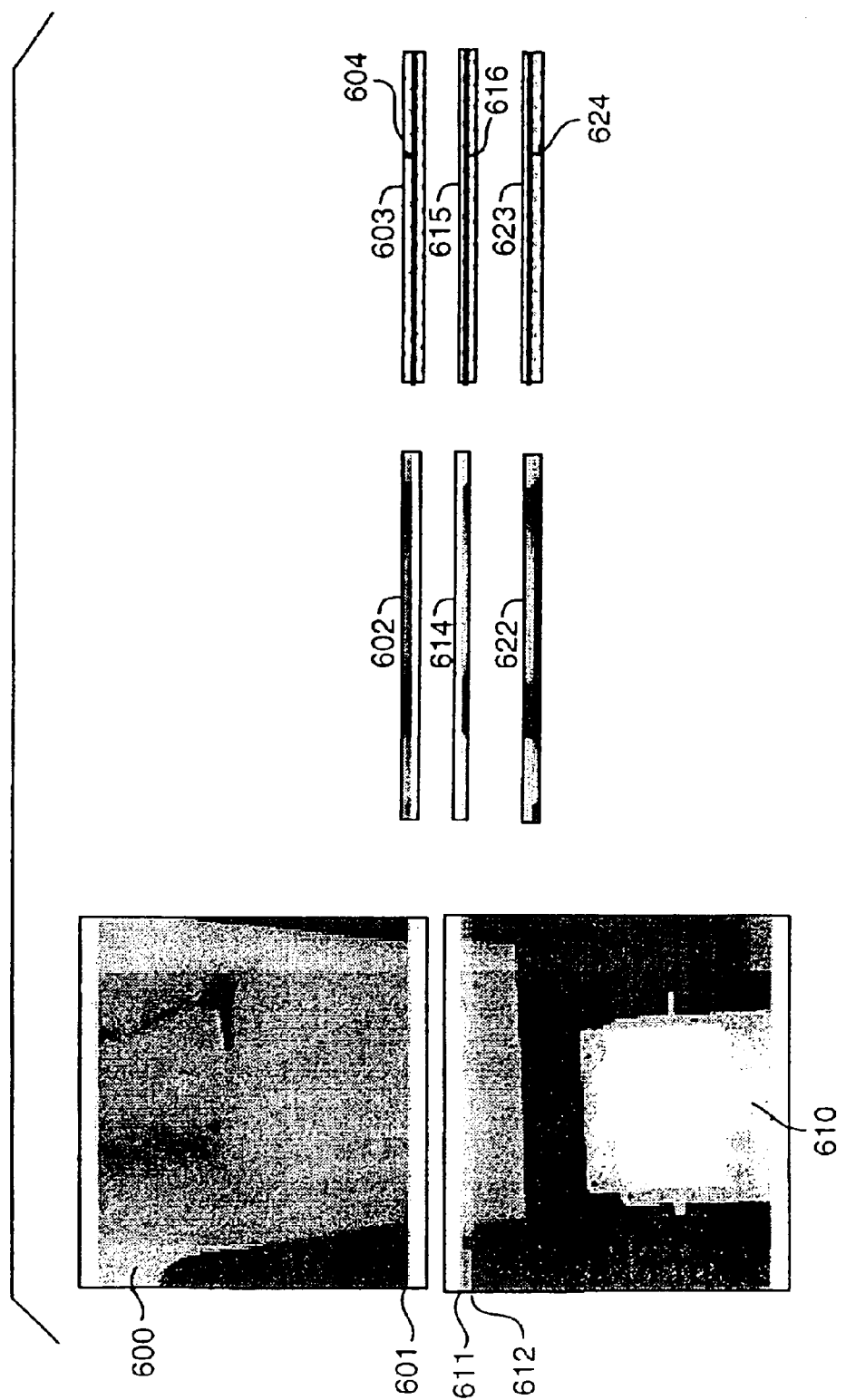

FIG. 6 is a diagrammatic view illustrating the major image processing steps that are used to automatically find the locations and orientations of the screen overlap edges in both the front and the back images, and for finding the location and orientation of the shadow of the front screen overlap edge in the back image.

Figure 7:
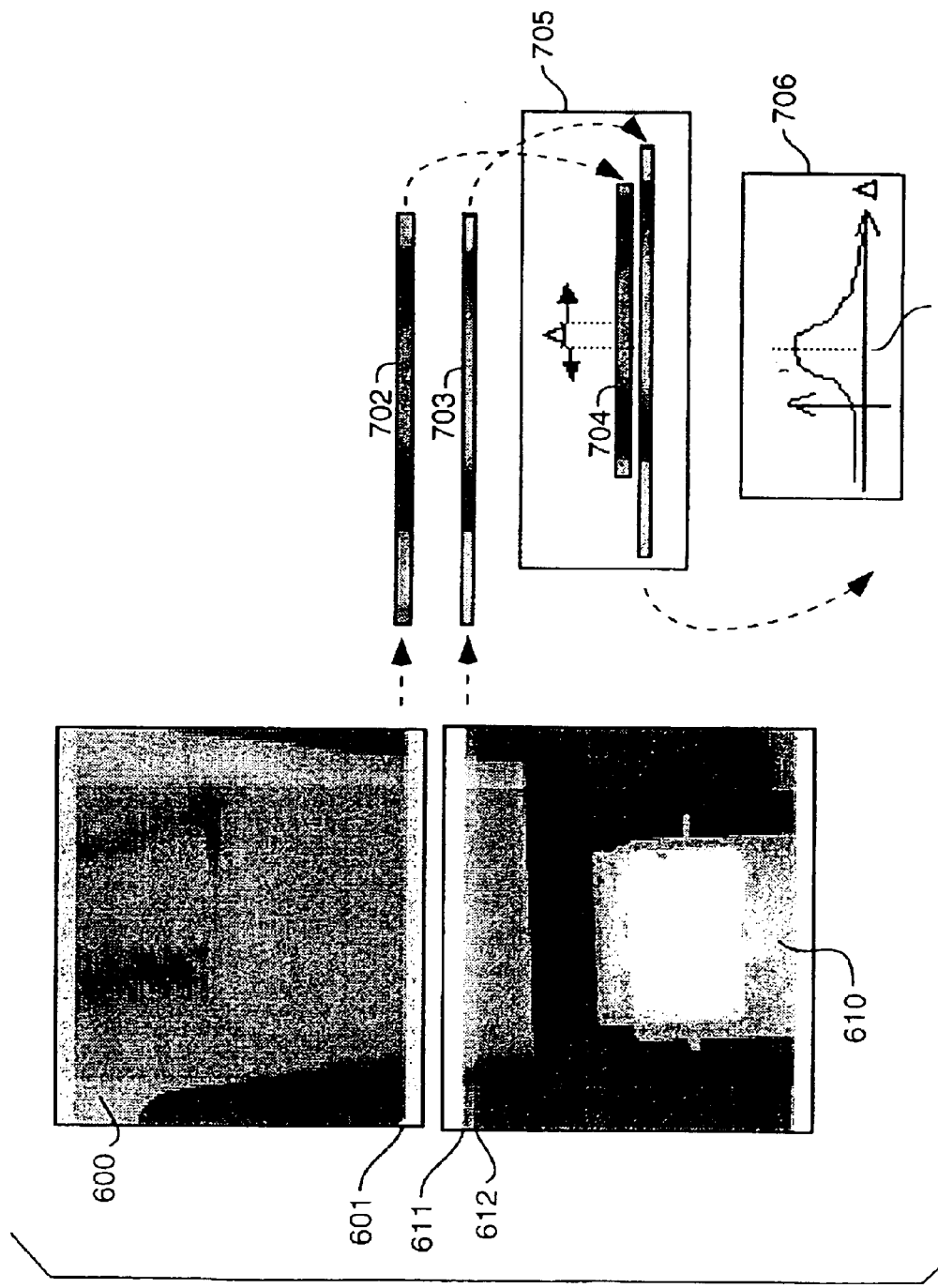

FIG. 7 is a diagrammatic view illustrating the major image processing steps that are used for finding the horizontal displacement between the front and back images by image-correlation.

Figure 8A:
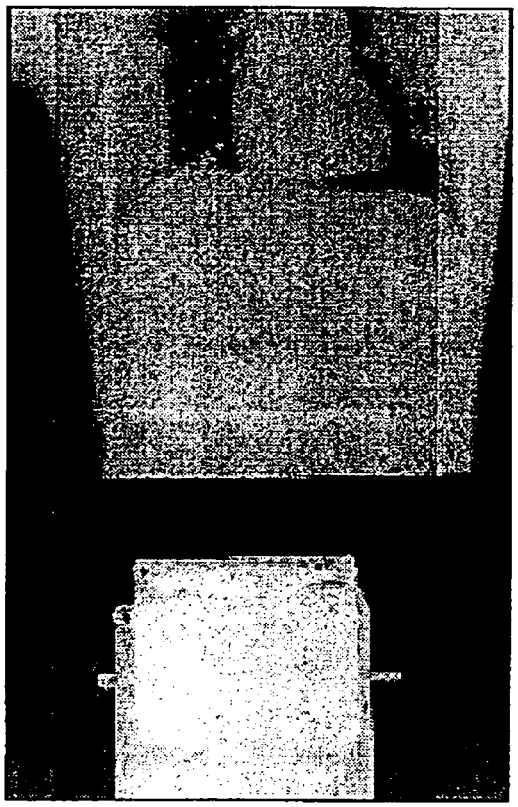
Figure 8B:
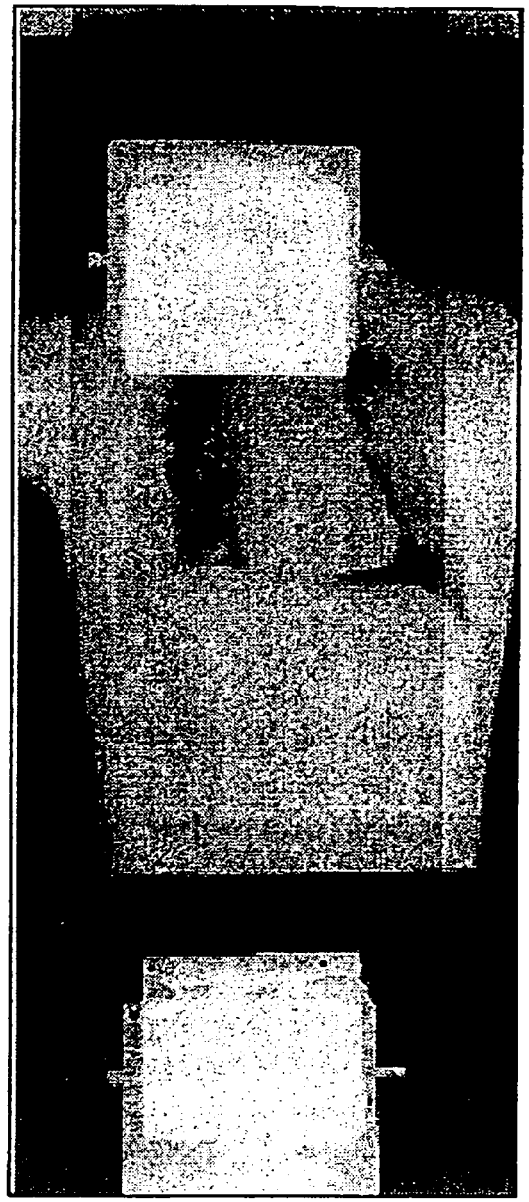

FIGS. 8A and 8B are diagrammatic views showing examples of composite stitched images from two screens and three screens, respectively.

DETAILED DESCRIPTION OF THE INVENTION

In general, the present invention relates to the radiographic imaging of an elongated object such as the full spine, e.g., for diagnosing scoliosis, or leg of a human subject.

US Patent Application by Brahm, Odea, Rogers, Wang proposes a method that is a hybrid between the cassette stacking and storage phosphor screen stacking methods. As shown in FIG. 1G, cassettes and storage phosphor screens are placed in a partially overlapping and alternating arrangement with the screens always positioned in front of the cassettes. This method eliminates the cassette metallic frame shadow from the acquired images, and reduces the number of storage phosphor screens that need to be removed out of and to be replaced back into cassettes.

When an x-ray exposure is taken with any of the cassette/phosphor screen setups shown in FIGS. 1A–1G, a plurality of sub-images is obtained, each of which bears a partial image of the elongated object. Because the phosphor screens are the fundamental imaging recording devices, no matter whether the screens are packaged within individual cassette or not, the term "storage phosphor screen", "phosphor screen", or "screen" is used hereinafter to represent either the phosphor screen itself or the phosphor screen that is conveyed inside a cassette. Therefore the different scenarios in FIG. 1 are reduced to alternating, staircase-wise, and oblique arrangements of overlapping phosphor screens, with the exception that the distance between the screen planes can vary for each scenario depending on if the screen(s) is contained inside the cassette or not.

Figure 2:
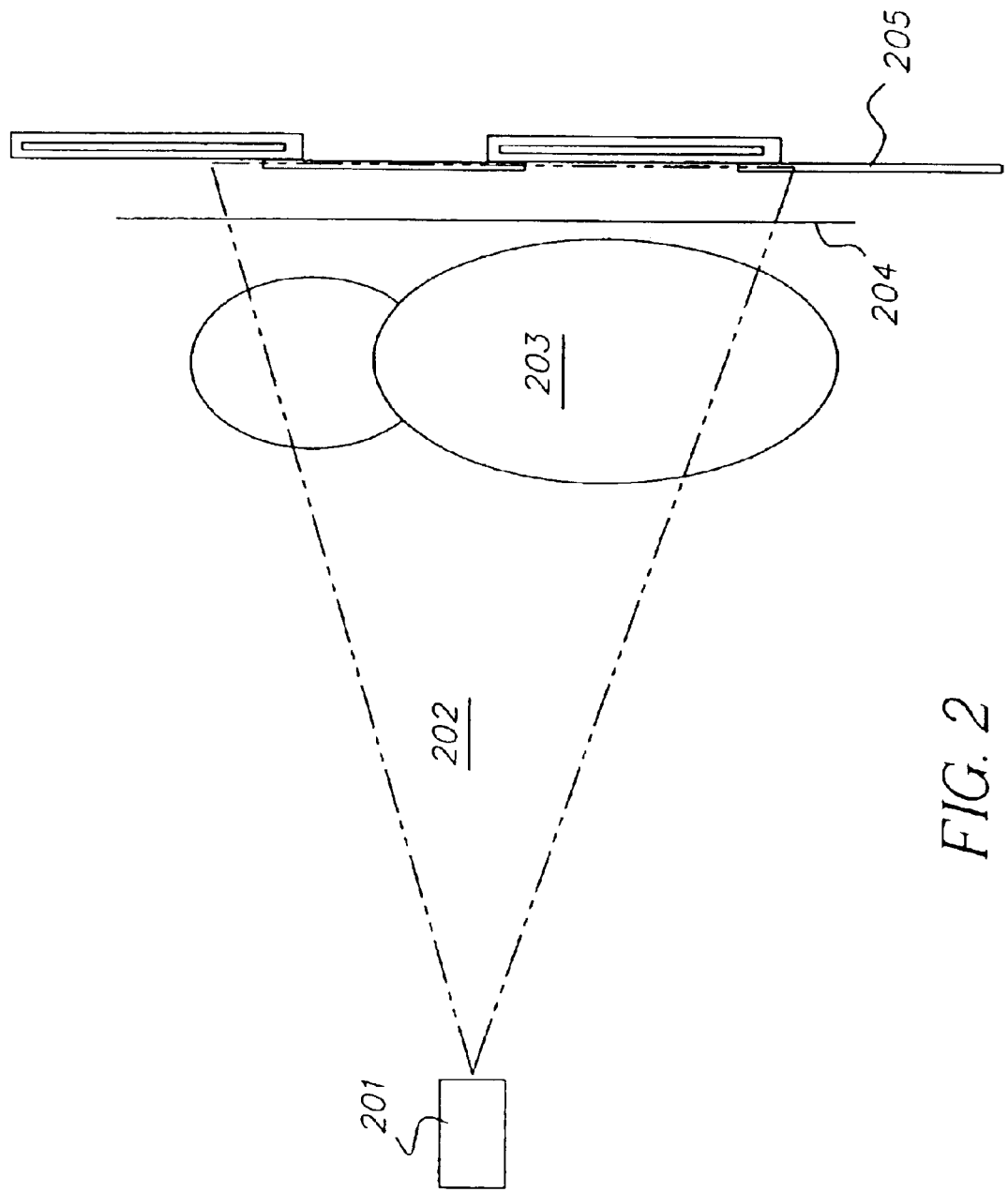
FIG. 2 is a diagrammatic view showing the method for image acquisition using the alternating phosphor screen/cassette configuration shown in FIG. 1G as an example. Any of the other configurations shown in FIG. 1 can also be used for acquiring the images.

FIG. 2 shows the process for conducting an x-ray exposure. The patient (element 203) is positioned between the x-ray source (element 201) and a plurality of screens (element 205). Any of the screen arrangement methods shown in FIGS. 1A–1G can be used for imaging. An optional anti-scatter grid (element 204) can be placed between the patient and the screens. The grid can be either a stationary type or reciprocating type. During x-ray exposure, the x-rays can be collimated to minimize the radiation to the non-diagnostically relevant patient anatomy. After the x-ray generator is fired and the cassette is exposed, the image of the patient is recorded by the plurality of screens as latent radiographic signals. Each screen captures only a portion of the image of the patient. The screens are fed into a CR reader and the latent radiographic signals are converted to electronic images.

FIG. 3A shows an example for the case where three storage phosphor screens are exposed. The two phosphor screens that capture the first image (element 301) and the third image (element 303) are placed behind the screen that captures the second image (element 302). Because the first screen 301 and the second screen 302 partially overlap, and the second screen 302 is not totally opaque to the incident x-rays, the first screen 301 still captures the image of the patient in the screen overlap region (element 307). However, the signal-to-noise ratio of the image captured on the first screen 301 in the overlap region will be relatively lower because of the x-ray attenuation caused by the second screen 302. The top edge of the second screen 302 also imposes a distinct shadow in the first image, as indicated by element 305. Similarly, the bottom edge of the second screen 302 imposes a shadow in the third image, as indicated by element 306 in screen 303. In all three images, the boundaries between the collimated and non-collimated exposure regions are indicated by element 304.

The relationship between any two consecutive screens is equivalent for the screen configurations shown in FIGS. 1A–1G. The screens partially overlap and one screen is positioned closer to the x-ray source. The term "front screen" will be used to refer to the screen that is positioned closer to the x-ray source, and the term "front image" will be used to refer to the image captured with the front screen. Similarly, the terms "back screen" and "back image" are used to refer to the screen that is positioned further from the x-ray source and "back image" will refer to the image captured with the "back screen". When a group of N screens are used for an x-ray exposure (N>=2), the screens can be divided into N-1 screen pairs, each of which consists of two consecutive screens—one front screen and one back screen. By this definition, one screen can be the front screen in one "screen pair", and can also be the back or the front screen in the next screen pair. The problem of reconstructing a composite full image consists of stitching the front and back images acquired with a screen pair. Once the first pair of images is stitched, the resultant composite image is grouped with the next consecutive image into a new front/back image pair. The same stitching method is used again and a new larger composite image is created. This process is repeated until all the images are stitched together. In the following description of the invention, the term "vertical" is used to mean the direction in which the phosphor screens are stacked and the term "horizontal" is used to mean the direction perpendicular to the "vertical". It will be understood that the screens can be oriented in any direction during x-ray exposure.

FIGS. 4A and 4B illustrate additional terminology used in this invention description, where the front and back screen overlap edges are indicated 110 by elements 406 and 407. In the present invention, the generation of a full composite image from the set of images captured with a plurality of screens that are in any of the arrangements of FIG. 1 is comprised of the following steps: (1) selection of a first pair of consecutive images, which consist of a front image and a back image, (2) demagnification of image pixels if applicable based on the distance between the x-ray source and the phosphor screens, (3) determination of the rotational displacement and the vertical displacement between the front and back images by matching the front screen overlap edge in the front image to its shadow in the back image, (4) image orientation correction if applicable based on the rotational displacement, (5) determination of the horizontal displacement between the front and back images by correlating the image information in the overlapping screen regions, and (6) stitching the front and the back images together to create a larger composite image along the front screen overlap edge based on the horizontal and vertical displacements, and (7) repeat steps 2–6 with the larger composite image and the next consecutive image until all the images are stitched together.

In order that the front screen overlap edge be completely present in the front image, which is usually not available or guaranteed in a conventional CR reader, the CR reader should be capable of over-scanning the front phosphor screen beyond the overlap edge. Using the modified image in FIG. 3B as an example, the top and bottom edges of the phosphor screen are over-scanned, the resultant image is indicated by element 310, and the top and bottom edges are completely visible (elements 311 and 312). The location and orientation of edges 311 and 312 will be compared to the corresponding shadows (elements 305 and 306 in FIG. 3A), based on how the relative orientation and vertical displacement between the first and second images as well as the second and third images are computed.

FIG. 5 is a flowchart that describes the key steps of this invention using a CR reader that overscans both the top and bottom edges of all the phosphor screens. It is understood that many variations can be derived based on the spirit of this invention.

Image de-magnification is performed in elements 505–508 after a patient is exposed (box 500), and a plurality of storage phosphor screens is read and digitally stored to create images 1 . . . N (N>=2). There is a slight screen location dependent, geometric distortion (magnification) introduced to the captured images because the phosphor screens are not exactly co-planar. The further the screen from the x-ray source, the greater the magnification factor. For example, using 180 cm as the reference distance from the x-ray source to the screen, an image acquired with the screen placed at 181 cm will be 0.6% larger. This distortion impacts the stitching precision and if not corrected may introduce a discontinuity adjacent to the seam line in the stitched image. It is therefore necessary to perform image de-magnification. This correction becomes more important as the source-to-screen distance is decreased. To correct for the magnification distortion, a virtual reference detector plane is defined and all the captured images are normalized to this plane. This reference detector plane can be defined anywhere in the x-ray path, such as the anti-scatter grid surface plane. The equations to de-magnify an image and normalize the de-magnified image to the virtual detector plane are given by:

$$x'=gx,$$

$$y'=gy,$$

$$g=D/D_0. \qquad (1)$$

The parameters x and y are image pixel coordinates in the vertical and horizontal axes, respectively; x' and y' are the new image pixel coordinates, respectively g is a constant; and $D_0$ and D respectively are the distances from the x-ray source to the reference detector plane and the distance from the x-ray source to the physical storage phosphor screen that captures the image. As shown in FIG. 2, the reference detector plane (RDP) coincides with the plane of the front storage phosphors and the back storage phosphor plane (SPP) coincides with the plane of back storage phosphors. The distance $D_0$ and D are the same for the front storage phosphor plane and different for the back storage phosphor plane.

This group of equations is applicable for all the screen configurations shown in FIG. 1A–1G except FIGS. 1C and 1F, where the distance from the x-ray source to the screen varies, and consequently the magnification factor varies gradually from top to bottom. A new set of formulas must be used for this configuration:

$$x'=g(x) \times x,$$

$$y'=g(x) \times y,$$

$$g(x)=((D_b-D_t) \times (x-x_{min})/(x_{max}-x_{min})+D_t)/D_0 \qquad (2)$$

The parameters $D_t$ and $D_b$ are the distances from the x-ray source to the top and the bottom of screen, respectively; $x_{min}$ and $x_{max}$ are the minimum and maximum image pixel coordinate in the vertical axis. Equation 2 ensures that each image pixel is remapped to the reference detector plane based on its physical distance from the x-ray source. The amount of computation for image demagnification can be reduced nearly in half for the screen setups in FIGS. 1A, 1D, and 1G by defining the reference detector plane to be located at the same position as the screens that are positioned closer to the x-ray source. Using this reference detector plane location causes the g factor in equation 1 to have a value of 1, i.e., no demagnification is required for the front images. This demagnification step can be totally eliminated when the x-ray source to the phosphor screens becomes much larger than the distance between the screens, as the distortion introduced by the magnification factor is negligible.

The next step Element 509 (FIG. 5) is to identify the front and back images acquired with two consecutive screens. In order to calculate the parameters that are used for stitching the front and back image, the screen overlap edges must be located correspondingly from the front and back images (element 510, 511). The shadow of the front screen overlap edge is then detected in the back image (element 512). These steps are further illustrated in FIG. 6. The pixel values in the image region that is beyond the screen overlap edge reflect the baseline noise level of the CR reader. This is because there is no signal contribution from the phosphor screen. Consequently, the pixel values in these regions are relatively low in comparison to those in the normally exposed image regions, therefore there is an abrupt pixel value decrement/discontinuity across the screen overlap edge in the image. This pixel value discontinuity is used to detect the location and orientation of the screen overlap edges, which can be accomplished in many ways. In the preferred embodiment of the present invention, the detection is carried out by (1) computing all the significant edge transition pixels in the proximity of the screen overlap edge, and (2) performing line delineation of the candidate transition pixels of the screen overlap edge.

Using the front image as an example, FIG. 6 describes the preferred embodiment of the detection process. First, a narrow band 602 is extracted from the end of the front image 600. Depending on how the phosphor screen is being scanned in the CR reader, the orientation of the screen ending edge 601 can have a variation of several degrees in the acquired image from one scan to the next scan. Therefore, the size of the narrow band must be large enough such that the entire screen ending edge can be reliably extracted. For an image that has a width of 2,048 pixels, the size of the narrow band should be approximately 200×2,048 pixels.

Second, the one-dimensional derivative of the image is computed in the vertical direction. A one-dimensional derivative operator, such as [−1,0,1], [−1,0,0,0,1], or [−1,0,0,0,0,] etc., is preferred because the pixel value discontinuity only occurs across the edge direction, which is always nearly horizontal, and because of the computational efficiency advantages. A predefined threshold is used to select only those candidate edge transition pixels that are of greater magnitude and of falling slope. Element 603 shows the results from this step.

Third, a linear function is fitted to the candidate edge pixels and the best fitting parameters are obtained when the least square error is reached. Element 604 shows the fitted linear function overlaid on top of the edge transition pixels. The fitting parameters describe the ending edge location and orientation:

$$x=k_f \times y+a_f, \quad (3)$$

where $a_f$ and $a_f$ are the fitting parameters with $k_f$ the orientation and $a_f$ the offset of the front screen overlap edge in the front image. Similarly, this process is conducted for the back image 610, except rising edge transition pixels are searched instead inside a narrow band 614 at the beginning of the back image. A new function is obtained by least-square-error fit:

$$x=k_b \times y+a_b, \quad (4)$$

where $k_b$ and $a_b$ are the fitting parameters with $k_b$ the orientation and $a_b$ the offset of the back screen overlap edge in the back image. Element 616 shows the fitted linear function overlaid on top of the edge transition pixels.

Once the screen overlap edge location is successfully found in the front image, it is compared with its shadow in the back image for image registration. To locate the shadow of the front screen overlap edge in the back image, an approach similar to element 511 is used. This is possible because the pixel values in the back image also undergo a strong signal intensity decrement in the screen overlap region due to the high attenuation of the incident x-rays by the front screen during the x-ray exposure. In order to locate the shadow of the front screen overlap edge, the location of the narrow band needs to be defined in the back image. This can be calculated based on the size of the overlap regions (S in mm), which is a priori, the image pixel size (psize in mm), and the average location of the identified back screen overlap edge. The distance from the center of the narrow band to the beginning of the back image is given by:

$$d=S/psize+(k_b \times y_c+a_b). \quad (5)$$

where $y_c$ is the center image pixel coordinate in the horizontal axes. The function that is obtained using the least-square-error fit to describe the shadow of the front screen overlap edge in the back image can be depicted as:

$$x=k \times y+a, \quad (6)$$

where k and a are the fitting parameters with k the orientation and a the offset. (See elements 622, 623, and 624 in FIG. 6).

Theoretically, parameters $k_f$ and k should be equal because they both represent the orientation of the front screen overlap edge. However, they may differ by as much as several degrees in practice for several reasons such as misalignment between the two phosphor screens during the x-ray exposure or screen positioning variations in the CR reader during the readout process. The deviation between $k_f$ and k represents the orientation misalignment between the front and back images. To assure a seamless composite image after stitching, and to preserve high geometric fidelity, this misalignment must be corrected. However, the correction can be ignored if the misalignment is fairly small. For example, in the case when it only generates a maximum of several pixel gap i.e., $k_f - k \times y_{max} < 3$ where $y_{max}$ is the maximum image pixel coordinate in the horizontal direction.

Misalignment correction is accomplished by rotating either the front or the back image. If the front image is to be rotated, the rotation angle is $\theta = \text{atan}(k) - \text{atan}(k_f)$, if the back image is to be rotated, the angle is $\theta = \text{atan}(k_f) - \text{atan}(k)$, or if both images are to be rotated, the angle is $-\text{atan}(k_f)$ and $\text{atan}(k)$ respectively for the front and back images. Element 513 (FIG. 5) represents the process for calculating the rotational angle and the calculation of the vertical displacement. Element 514 (FIG. 5) represents the image rotation operation. Since the parameters that are used for aligning the front and back images, e.g., $k_a$, $k_b$, k, $a_a$, $a_b$, and a, are calculated before image rotation, they must be transformed accordingly to reflect their new values in the rotated image (s). The parameters are modified by placing Eq. 3, 4, and 6 into the transforms given by:

$$x'=x \cos \theta + y \sin \theta,$$

$$y'=-x \sin \theta + y \cos \theta, \quad (7)$$

where (x', y') are the new coordinates in the rotated image, and θ is the rotation angle. For the simplicity of the description, the symbols $k_a$, $k_b$, k, $a_a$, $a_b$, and a will be used to represent the new transformed values.

The vertical displacement between the front and back image, x_offset, is defined as the vertical distance from each pixel in the back image to origin of the front image and is given by:

$$x\_offset = a_f - a_b. \quad (8)$$

Using the vertical displacement guarantees that the front and the back images are stitched along the overlap edge of the front screen.

Once the back screen overlap edge, as described by $k_b$ and $a_b$, and the shadow of the front screen overlap edge, as described by $k_a$ and $a_a$, are successfully identified, the location of the screen overlap region in the back image can be defined. The screen overlap region in the back image is located between the back screen overlap edge and the shadow of the front screen overlap edge. The size of the region is calculated based on the equation given by:

$$overlap\_size = (k \times y_c + a) - (k_b \times y_c + a_b), \quad (9)$$

and the vertical displacement from the back image origin is:

$$overlap\_offset_b = (k_b \times y_c + a_b). \quad (10)$$

Using the computed value of overlap_size, the corresponding region in the front image is derived. This is the region of the same size but with a vertical displacement from the image origin defined by:

$$overlap\_offset_f = x_{max} - (k_a \times y_c + a_a) - overlap\_size. \quad (11)$$

The process of extracting the image overlap regions is represented by element 515 (FIG. 5). After the screen overlap regions are extracted from both images, as shown by elements 702 and 703 in FIG. 7, they are compared in the next step (Element 516) to find the horizontal displacement or offset between the front and back images.

The image content recorded in the overlap regions are the same except for some horizontal displacement, y_offset, between the corresponding pixels. A one-dimensional correlation function is computed to find the displacement using the formula given by $$c(\Delta) = \Sigma_{i,j} F(x_i, y_j) \times B(x_i, y_j + \Delta), \quad (12)$$

where $F(x_i, y_j)$ and $B(x_i, y_j)$ is the pixel value at $(x_i, y_j)$ in the extracted overlap region from the front and back images, respectively, and Δ is the horizontal displacement parameter for correlation. The Δ value at which c(Δ) reaches a maximum is the optimal value for y_offset.

FIG. 7 describes the preferred implementation of this operation. First, the overlap region 702 and 703 are extracted from the front and back images respectively. Second, element 704 is obtained by extracting a portion of 702, then is correlated with 703 to create the correlation function c(Δ), 706. Similar results can be achieved by correlating a portion of 703 with 702. Third, the maximum of function c(Δ) is searched and the corresponding value of Δ is identified as y_offset, 707. Because the edge information in 702 and 703, including skin line, tissue boundaries, bone edges, collimation boundaries (element 304 in FIG. 3), and hardware labels etc, contribute the most useful information to the correlation, in a preferred embodiment of the present invention, the low frequency content is removed from 702 and 703 in order to improve the correlation robustness. It has been found that the presence of the collimation shadow (element 304) helps improve the algorithm robustness in finding y_offset Therefore, it is recommended to use collimation during the x-ray exposure. Normally the correlation function is smooth, but if a stationary grid is used during the x-ray exposure, it imposes a periodic line pattern artifact in the acquired images. This artifact is particularly dominant when the grid is orientated in the vertical direction, and can correlate with itself, causing periodic small spikes to be introduced on top of the background correlation function. This artifact will negatively impact the accuracy in determining the location of the true function maximum. To address this issue, low-pass filtering of the correlation function is used before searching for the maximum. The process described in this paragraph is represented by element 516 (FIG. 5).

After the front and the images have been demagnified and rotated if applicable, and x_offset and y_offset have been found, the back image is stitched to the front image. Each pixel of the front image is copied to the stitched image buffer except those pixels that are beyond the screen overlap edge line. Each pixel in the back image is copied to the stitched image buffer with an displacement defined by x_offset and y_offset except those pixels before the shadow of the front screen overlap edge. The resultant larger image is shown in FIG. 8A. The process conducted in this paragraph is represented by element 517 (FIG. 5).

Once the first two consecutive images are stitched, the resultant larger image will be grouped with a next consecutive image, and again, a front image and back image are identified, and the same processes from elements 509 to 517 (FIG. 5) are repeated until the last image is stitched (Element 518—FIG. 5). FIG. 8B shows a stitched image acquired with three screens. The composite full image is then outputted (Element 519—FIG. 5).

It will be understood that the invention may be applied to the stitching together of any number of over-lapped images produced by radiographic techniques. The invention would also be applicable to digital images resulting from overlapping conventional radiographic film images that have been digitized.

The invention has been described in detail with particular reference to certain preferred embodiments thereof, but it will be understood that variations and modifications can be effected within the spirit and scope of the invention.

| PARTS LIST | |
|---|---|
| 10 | storage phosphor cassette |
| 12 | elongated rectangular shell |
| 14 | first open end |
| 16 | second open end |
| 18 | first phosphor plate assembly |
| 20 | second phosphor plate assembly |
| 22, 24 | storage phosphor plate |
| 26, 28 | latching assembly |
| 29 | central region |
| 30, 32 | upper and lower members |
| 34, 36 | side extrusions |
| 40, 42 | inner surfaces |
| 44, 46 | deflectors |
| 201 | x-ray source |
| 202 | x-ray beam coverage |
| 203 | object/patient for imaging |
| 204 | x-ray antiscatter grid |
| 205 | a plurality of storage phosphor screens/cassettes for image |

-continued

PARTS LIST

| | | |
|---|---|---|
| | capture | |
| 301 | image 1 acquired with screen 1 | |
| 302 | image 2 acquired with screen 2, which is closer to the x-ray source than screen 1 and screen 3 | |
| 303 | image 3 acquired with screen 3 | |
| 304 | boundaries between collimated/no-collimated image regions | |
| 305 | top edge shadow of screen 2 in image 3 | |
| 306 | bottom edge shadow of screen 2 in image 3 | |
| 307 | screen 1 and screen 2 overlap region in image 1 | |
| 308 | screen 2 and screen 3 overlap region in image 3 | |
| 310 | image 2 that is obtained with CR overscan | |
| 311 | screen 2 top edge in overscanned image | |
| 312 | screen 2 bottom edge in overscanned image | |
| 401 | x-ray source | |
| 402 | front screen - lateral view | |
| 403 | back screen - lateral view | |
| 404 | front screen - front view | |
| 405 | back screen - front view | |
| 406 | back screen overlap edge | |
| 407 | front screen overlap edge | |
| 500 | expose object/patient with x-rays | |
| 501 | read/store first image | |
| 502 | read/store second image | |
| 503 | read/store third image | |
| 504 | read/store Nth image (N >= 2) | |
| 505 | demagnification of image 1 | |
| 506 | demagnification of image 2 | |
| 507 | demagnification of image 3 | |
| 508 | demagnification of image N | |
| 509 | identify front and back image from a pair of consecutive images | |
| 510 | detect front screen overlap edge in front image | |
| 511 | detect back screen overlap edge in back image | |
| 512 | detect shadow of front screen overlap edge in back image | |
| 513 | calculate vertical offset and rotational displacement | |
| 514 | image rotation | |
| 515 | extract image overlap regions from both front and back images | |
| 516 | calculate horizontal offset between front and back images | |
| 517 | stitch two image together to create a larger image | |
| 518 | determine if more images need to be stitched | |
| 519 | output final stitched image | |
| 600 | acquired front image | |
| 601 | front screen overlap edge | |
| 602 | extracted narrow band at the end of front image for identifying screen overlap edge | |
| 603 | candidate edge transition pixels (falling slope) in 602 | |
| 604 | fitted line overlaid on top of candidate edge transition pixels | |
| 610 | acquired back image | |
| 611 | back screen overlap edge | |
| 612 | shadow of front screen overlap edge in the back image | |
| 614 | extracted narrow band at the beginning of back image for identifying screen overlap edge | |
| 615 | candidate edge transition pixels (rising slope) in 614 | |
| 616 | fitted line overlaid on top of candidate edge transition pixels | |
| 622 | extracted narrow band for searching of shadow of front screen overlap edge | |
| 623 | candidate edge transition pixels (rising edge) in 622 | |
| 624 | fitted line overlaid on top of candidate edge transition pixels | |
| 702 | extract screen overlap region from front image | |
| 703 | extracted screen overlap region from back image | |
| 704 | a portion of 702 | |
| 705 | process for conducting image correlation | |
| 706 | correlation function | |
| 707 | the location of maximum in the correlation function | |

What is claimed is:

1. A method of forming a composite digital image comprising:

providing 1–N digital images formed from 1–N contiguous segments of a larger radiographic image recorded in 1–N overlapping storage phosphor screens wherein N is equal to or greater than 2 and wherein the image content in the overlapped region of contiguous images is the same, and an end edge of a screen nearest an x-ray source is present in both contiguous images;

selecting a pair of contiguous digital images, wherein one image of the pair is closer to said x-ray source than an other image of the pair;

correcting for any geometric distortion if applicable in said pair of digital images based on the distance between x-ray source and said storage phosphor screen;

determining any rotational displacement and any vertical displacement between said pair of digital images by matching an end edge of said one image present in said pair of images;

correcting for image orientation if applicable based on any said rotational displacement;

determining any horizontal displacement between said pair of digital images by correlating the image content in said overlapping regions of said pair of digital images;

stitching said pair of digital images together to form a larger composite digital image along said one image edge based on any said horizontal and vertical displacement; and repeating said correcting for any geometric distortion to said stitching with the larger composite image and the next consecutive overlapping digital image until all N digital images are stitched together to form a full composite image, wherein, at the time of recording, said overlapping storage phosphor screens are contained in staggered cassettes that are staggered in an alternating arrangement or an oblique arrangement.

2. The method of forming a composite digital image comprising:

providing 1–N digital formed from 1–N contiguous phosphor screens wherein N is equal to or greater than 2 and wherein the image content in the overlapped region of contiguous images is the same, and an end edge of a screen nearest an x-ray source is present in both contiguous images;

selecting a pair of contiguous digital images, wherein one image of the pair is closer to said x-ray source than an other image of the pair;

correcting for any geometric distortion if applicable in said pair of digital images based on the distance between x-ray source and said storage phosphor screen;

determining any rotational displacement and any vertical displacement between said pair of digital images by matching an end edge of said one image present in said pair of images;

correcting for image orientation if applicable based on any said rotational displacement;

determining any horizontal displacement between said pair of digital images by correlating the image content in said overlapping regions of said pair of digital images;

stitching said pair of digital images together to form a larger composite digital image along said one image edge based on any said horizontal and vertical displacement; and repeating said correcting for any geometric distortion to said stitching with the larger composite image and the next consecutive overlapping digital image until all N digital images are stitched together to form a full composite image, wherein, at the time of recording, said overlapping storage phosphor screens are contained in a single cassette in one of (a) an alternating arrangement, (b) a staircase-wise arrangement, or (c) an oblique arrangement.

3. A method of forming a composite digital image comprising: providing 1–N digital images formed from 1–N contiguous segments of a larger radiographic image recorded in 1–N overlapping storage phosphor screens wherein N is equal to or greater than 2 and wherein the image content in the overlapped region of contiguous images is the same, and an end edge of a screen nearest an x-ray source is present in both contiguous images;
  selecting a pair of contiguous digital images, wherein one image of the pair is closer to said x-ray source than an other image of the pair;
  correcting for any geometric distortion if applicable in said pair of digital images based on the distance between x-ray source and said storage phosphor screen;
  determining any rotational displacement and any vertical displacement between said pair of digital images by matching an end edge of said one image present in said pair of images;
  correcting for image orientation if applicable based on any said rotational displacement;
  determining any horizontal displacement between said pair of digital images by correlating the image content in said overlapping regions of said pair of digital images;
  stitching said pair of digital images together to form a larger composite digital image along said one image edge based on any said horizontal and vertical displacement; and
  repeating said correcting for any geometric distortion to said stitching with the larger composite image and the next consecutive overlapping digital image until all N digital images are stitched together to form a full composite image,
  wherein at the time of recording, said overlapping storage phosphor screens are arranged so that alternating screens are contained in cassettes and screens intermediate said cassettes directly overlap said cassettes.

4. The method of claim 3 wherein in forming a digital image from a radiographic image recorded in a storage phosphor screen, said screen is overscanned so that the top and bottom edges of said screen are visible in said digital image.

5. The method of claim 3 wherein said correcting for any geometric distortion is a function of the distance of each said storage phosphor screen from said x-ray source.

6. The method of claim 3 wherein said digital image includes a matrix of pixels and wherein said edge of said screen nearest said x-ray source is detected by detecting pixel value discontinuity in said overlap regions of said digital images.

7. The method of claim 6 wherein said detecting is carried out by computing all the significant edge transition pixels in the proximity of the screen overlap edge and performing line delineation of the candidate pixels of the screen overlap edge.

8. The method of claim 6 wherein said detecting is carried out by extracting a narrow band of pixels from the overlapping end of the front image, computing a one-dimensional derivative of the narrow band of pixels in the vertical direction, and fitting a linear function to the candidate edge pixels and the best fitting parameters are obtained when the least square error is readied.

9. The method of claim 8 wherein in said computing one of the operator (a) [−1,0,1], (b) [−1,0,0,0,1], or (c) [−1,0,0, 0,0,0,1] is used.

10. The method of claim 3 wherein said correcting the image for image orientation is carried out by one of (a) rotating said one digital image while keeping said other digital image unchanged, (b) rotating said other digital image while keeping said one digital image unchanged, or (c) rotating both said digital images relative to each other.

11. The method of claim 3 wherein said determining any horizontal displacement is carried out (a) by defining and extracting the image overlap region from said one digital image, (b) by defining and extracting the image overlap region of said other digital image and (c) calculating any horizontal displacement by finding maximum of image correlation function.

12. The method of claim 11 wherein said image correlation function is computed after the low frequency content is removed from both said image overlap regions.

13. The method of claim 11 wherein said calculating includes low-pass filtering of said correlation function.

14. The method of claim 11 wherein said calculating relies on edge information in said overlap regions, including skin line, tissue boundaries, bone edges, collimation boundaries, and hardware labels.

15. The method of claim 3 wherein in forming a digital image from a radiographic image recorded in a storage phosphor screen, said screen is over-scanned so that at least one edge of said screen is visible in said digital image.

16. A method of forming a composite digital image comprising:
  providing 1–N digital images formed from 1–N contiguous segments of a larger radiographic image recorded in 1–N overlapping storage phosphor screens wherein N is equal to or greater than 2 and wherein the image content in the overlapped region of contiguous images is the same, and an end edge of a screen nearest an x-ray source is present in both contiguous images;
  selecting a pair of contiguous digital images, wherein one image of the pair is closer to said x-ray source than an other image of the pair;
  correcting for any geometric distortion if applicable in said pair of digital images based on the distance between x-ray source and said storage phosphor screen;
  determining any rotational displacement and any vertical displacement between said pair of digital images by matching an end edge of said one image present in said pair of images;
  correcting for image orientation if applicable based on any said rotational displacement;
  determining any horizontal displacement between said pair of digital images by correlating the image content in said overlapping regions of said pair of digital images;
  stitching said pair of digital images together to form a larger composite digital image along said one image edge based on any said horizontal and vertical displacement; and
  repeating said correcting for any geometric distortion to said stitching with the larger composite image and the next consecutive overlapping digital image until all N digital images are stitched together to form a full composite image,
  wherein said correcting for any geometric distortion is a function of the distance of each said storage phosphor screen from said x-ray source, and wherein a reference detector plane is defined at a pre-selected distance from said x-ray source and wherein all the digital images are normalized to this plane.

17. The method of claim 16 wherein said reference detector plane coincides with the plane of one of said screens.

18. The method of claim 16 wherein said reference detector plane coincides with the plane of said screen(s) located closest to said x-ray source.

19. The method of claim 16 wherein said reference detector plane coincides with a front plane of an anti-scatter x-ray grid.

20. A method of forming a composite digital image comprising:

providing 1–N digital images formed from 1–N contiguous segments of a larger radiographic image recorded in 1–N overlapping storage phosphor screens wherein N is equal to or greater than 2 and wherein the image content in the overlapped region of contiguous images is the same, and an end edge of a screen nearest an x-ray source is present in both contiguous images;

selecting a pair of contiguous digital images, wherein one image of the pair is closer to said x-ray source than an other image of the pair;

correcting for any geometric distortion if applicable in said pair of digital images based on the distance between x-ray source and said storage phosphor screen;

determining any rotational displacement and any vertical displacement between said pair of digital images by matching an end edge of said one image present in said pair of images;

correcting for image orientation if applicable based on any said rotational displacement;

determining any horizontal displacement between said pair of digital images by correlating the image content in said overlapping regions of said pair of digital images;

stitching said pair of digital images together to form a larger composite digital image along said one image edge based on any said horizontal and vertical displacement; and repeating said correcting for any geometric distortion to said stitching with the larger composite image and the next consecutive overlapping digital image until all N digital images are stitched together to form a full composite image, wherein at the time of recording, collimation is used such that collimation shadow present in said digital images to improve the robustness of said determining any horizontal displacement.

* * * * *

UNITED STATES PATENT AND TRADEMARK OFFICE
CERTIFICATE OF CORRECTION

PATENT NO. : 6,895,106 B2
DATED : May 17, 2005
INVENTOR(S) : Xiaohui Wang et al.

It is certified that error appears in the above-identified patent and that said Letters Patent is hereby corrected as shown below:

Column 12,
Line 34, after "digital" insert -- images --; and after "contiguous" insert -- segments of a larger radiographic image recorded in 1-N overlapping storage --.

Signed and Sealed this

Twenty-second Day of November, 2005

JON W. DUDAS
*Director of the United States Patent and Trademark Office*